United States Patent [19]

George

[11] Patent Number: 4,935,001

[45] Date of Patent: Jun. 19, 1990

[54] SWAB

[76] Inventor: Gary F. George, 406 Barclay, Grosse Pointe Farms, Mich. 48236

[21] Appl. No.: 191,692

[22] Filed: May 8, 1988

Related U.S. Application Data

[62] Division of Ser. No. 105,000, Oct. 6, 1987, abandoned.

[51] Int. Cl.$^5$ ............................................. A61M 35/00
[52] U.S. Cl. ......................................... 604/1; 401/176
[58] Field of Search ............................. 604/1; 401/176

[56] References Cited

FOREIGN PATENT DOCUMENTS 451978 10/1948 Canada ................................. 401/176
0089271 9/1983 European Pat. Off. ................ 604/1

Primary Examiner—John D. Yasko
Attorney, Agent, or Firm—Gifford, Groh, Sprinkle, Patmore and Anderson

[57] ABSTRACT

A swab for collecting and removing material from small openings. The swab includes an absorbent tip attached to an elongated rod. The absorbent tip has an outer surface with at least one recess in which material is collected.

3 Claims, 1 Drawing Sheet

U.S. Patent   Jun. 19, 1990   4,935,001
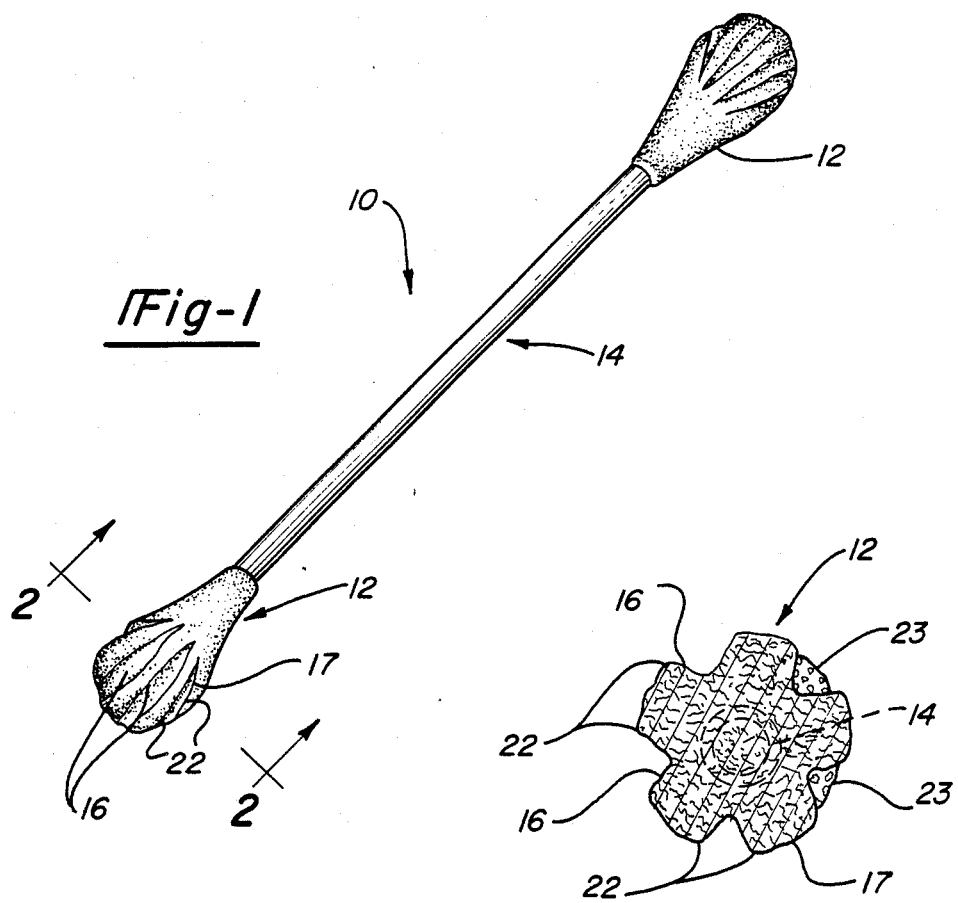
*Fig-1*
*Fig-2*
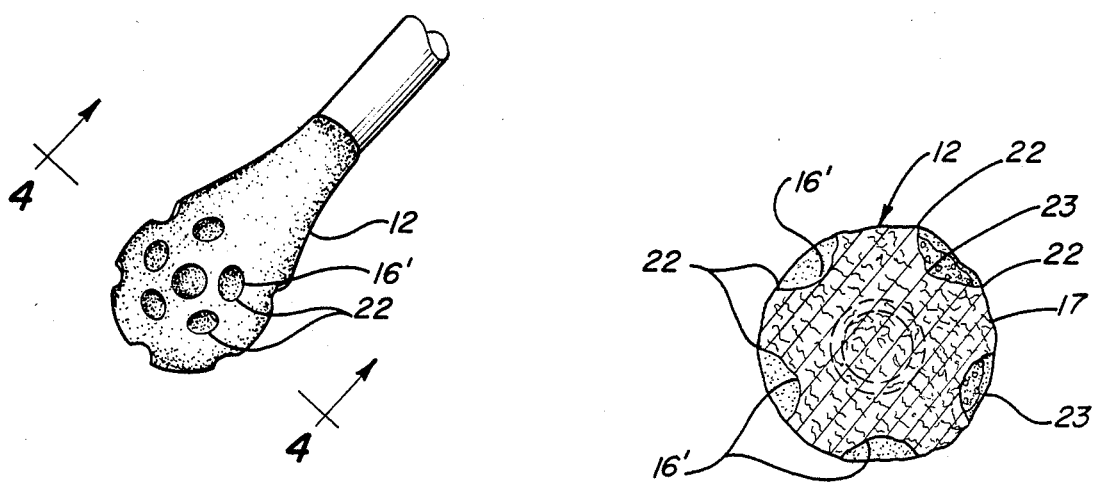
*Fig-3*
*Fig-4*

SWAB

This is a divisional of co-pending application Ser. No. 105,000, filed on Oct. 6, 1987, now abandoned.

BACKGROUND OF THE INVENTION

I. Field of the Invention

The present invention relates to swabs and, more particularly, to a swab for collecting and removing material from small openings.

II. Description of the Prior Art

Swabs are often used for collecting and removing material from small openings. These previously known swabs typically comprise an elongated rod having an absorbent tip attached to one end of the rod. The tip is oftentimes made of cotton and has a smooth outer surface. Such swabs are used, for example, to clean wax from the outer ear canal by inserting the tip into the ear canal and rotating it.

One disadvantage of these previously known swabs is that only a small amount of wax can be collected on the smooth outer surface of the tip. Consequently, it is necessary to use several swabs in order to completely clean the ear.

SUMMARY OF THE PRESENT INVENTION

The present invention provides a swab which overcomes the disadvantages of the previously known swabs.

In brief, the swab of the present invention comprises an elongated rod having an absorbent tip attached to at least one end, and preferably both ends, of the rod.

Unlike the previously known swabs, the absorbent tip contains at least one recess in its outer surface. In use, the wax or other material which is collected and removed by the swab accumulates in the recess on the tip. Consequently, a much greater amount of wax or other material can be removed than with the previously known swabs.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which:

FIG. 1 is a perspective view illustrating a preferred embodiment of the present invention;

FIG. 2 is a crossectional view taken along line 2—2 in FIG. 1 and enlarged for clarity;

FIG. 3 is a perspective view illustrating a second preffered embodiment of the invention; and FIG. 4 is a crossectional view taken along line 4—4 in FIG. 3 and enlarged for clarity.

DETAILED DESCRIPTION OF THE PREFERRED EMBODIMENTS OF THE PRESENT INVENTION

With reference first to FIG. 1, a first preferred embodiment of the swab 10 of the present invention is thereshown and comprises an elongated rod 14 having an absorbent tip 12 attached to one end and preferably both ends of the elongated rod 14.

The rod 14 is preferably made of wood, plastic or paper and is relatively stiff. Conversely, the tip 12 is preferably made of cotton or synthetic fibers and is also preferably absorbent.

With reference now to FIGS. 1 and 2, a plurality of recesses 16 are formed in the outer surface 17 of the tip 12. As shown in FIG. 1, these recesses 16 preferably extend longitudinally along the tip 12 and are circumferentially spaced from each other. Any conventional means, such as pressing, can be used to form the recesses.

With reference to FIGS. 3 and 4, a second preferred embodiment of the invention is thereshown in which circular recesses 16' replace the elongated recesses of the FIG. 1 embodiment. Other shapes for the recesses can also be used without deviation from the scope or spirit of the invention.

In use, e.g. when used to clean wax from ears, the presence of the recesses 16 and/or 16' on the absorbent tip 12 is highly advantageous in several different respects. First, each recess 16 forms an edge 22 at its junction with the outer surface 17 of the tip 12. When the tip 12 is rotated, the edge 22 acts to scrape the wax off from the surface of the ear canal and forces the removed wax into the recesses 16 as shown at 23.

A further advantage of providing the recesses 16 on the tip 12 is that, since the wax is collected within the recesses 16 and/or 16', a much greater amount of wax can be removed by a single swab than with the previously known swabs having smooth outer surfaces.

There are, of course, many different uses for the swab 10. For example, the swab 10 can also advantageously be used to apply eye make-up. In this use, the eye powder is first placed into the recesses 16 by rotating the swab 10 in the eye powder. The person can then apply the powder to the eye lid by depositing the powder from the recesses 16 onto the eyelid.

From the foregoing, it can be seen that the swab of the present invention provides an inexpensive and yet highly effective swab.

Having described my invention, however, many modifications thereto will become apparent to those skilled in the art to which it pertains without deviation from the spirit of the invention as defined by the scope of the appended claims.

I claim:

1. A swab comprising:
   an elongated rod;
   a tip having an outer surface and a plurality of circular recesses disposed throughout said outer surface of a size sufficient to form a scraping edge; and
   means for attaching said tip to each of both ends of said rod.

2. The invention as defined in claim 1 wherein said recess is elongated and extends longitudinally along the outer surface of the tip.

3. The invention as defined in claim 1 wherein said recess comprises a plurality of grooves extending longitudinally along the outer surface of the tip.

* * * * *